United States Patent [19]

Alvarado et al.

[11] Patent Number: 5,300,306

[45] Date of Patent: Apr. 5, 1994

[54] TISSUE-EQUIVALENT MEMBRANE FROM BOVINE ESOPHAGEAL TISSUE

[76] Inventors: Carlos A. Alvarado, 2da. Calle, 3-31, Zona 1; Cesar A. Letona, 28 Calle, 11-14, Zona 11, Colonia Granai Tonwson II; Arturo A. Perez, 2da. Calle E, 8-81, Zona 15, Colonia Trinidad, all of Guatemala

[21] Appl. No.: 953,099

[22] Filed: Sep. 29, 1992

[51] Int. Cl.$^5$ .................. A61K 35/37; A01N 1/00
[52] U.S. Cl. ......................... 424/550; 435/1
[58] Field of Search ................ 435/1, 240.1; 424/550

[56] References Cited

U.S. PATENT DOCUMENTS

| | | |
|---|---|---|
| 4,299,819 | 11/1981 | Eisinger . |
| 4,446,124 | 5/1984 | Fox, Jr. et al. . |
| 4,485,096 | 11/1984 | Bell . |
| 4,902,508 | 2/1990 | Badylak et al. ............ 424/551 |
| 5,015,584 | 5/1991 | Brysk . |

OTHER PUBLICATIONS

Eldad et al *Burns* 13(3) 1987 pp. 173-180 Cultured epithelium as a skin substitute.
Cvek et al *Odontologisk Revy* 27(1) 1976 pp. 1-10 Antimicrobial effect of Root canal . . . .

*Primary Examiner*—David M. Naff
*Assistant Examiner*—Francisco C. Prats
*Attorney, Agent, or Firm*—Richard C. Litman

[57] ABSTRACT

A ready to use heterograft membrane for replacement of injured skin which is prepared by extraction of a mucous membrane from an esophagus of bovine origin. The tissue-equivalent membrane resulting from this process is applied on burns, cuts or wounds to protect the affected area and generally provide an optimum condition for the proliferation of epidermal cells. The membrane has an affinity with tissue cells and integrates to the living tissue. Afterwards, it falls off, leaving the wound area prepared for homografting, or when the epidermis has completely regenerated.

4 Claims, No Drawings

TISSUE-EQUIVALENT MEMBRANE FROM BOVINE ESOPHAGEAL TISSUE

BACKGROUND OF THE INVENTION

1. Field of the Invention

This invention relates to a process for producing a tissue-equivalent membrane for use on burns, cuts or other wounds to protect an affected part and provide an optimum condition for the proliferation of epidermal cells, and, more particularly, to a tissue-equivalent membrane prepared by extraction from an esophagus of bovine origin.

2. Description of the Prior Art

Wounds which involve injuries to significant areas of human skin are difficult to treat. Covering the wound is an important aspect to successful care, and is often limited by lack of suitable autograft material. Because of this limitation, several temporary coverings have been developed and used. However, none of these has achieved the total benefit which results from an autograft. Products used as temporary coverings include human allografts, xenografts (e.g., pigskin), and a variety of manufactured membranes. Examples of patents of this type include:

U.S. Pat. No. 4,299,819 issued on Nov. 10, 1981 to Magdelena G. Eisenger discloses a process for treating burn victims wherein human epidermal cells are grown in a tissue culture medium having a pH from about 5.6 to 5.8. The edges of the sheet thus grown are separated from the tissue vessel and then applied to a transfer member (a collagen sponge or dermal side of porcine origin is discussed, along with using the pateint's own skin). This aggregate is then applied to the wound site. The novelty in the disclosure is that only epidermal cells are used, which retain the ability to differentiate into multilayered structures.

U.S. Pat. No. 4,446,124 issued on May 1, 1984 to Charles L. Fox, Jr. et al. discloses a wound dressing comprising silver sulfadiazine incorporated in animal tissue wherein, to minimize the possibility of bacteria that might have entered the wound before the dressing is applied, the dressing is prepared by placing it in an aqueous solution containing ammoniacal silver sulfadiazine for a period of time. Alternatively, one could spray the dressing with the solution. After the ammoniated silver sulfadiazine is incorporated into the tissue matrix, the dressing is partially dried and stored in sterile circumstances for later use.

U.S. Pat. No. 4,485,096 issued on Nov. 27, 1984 to Eugene Bell discloses a tissue equivalent and method of preparation wherein a hydrated collagen lattice is formed in vitro and is used as a substrate for different types of tissue equivalents. Skin equivalent is formed by plating keratinocyte cells on this substrate. Small vessel equivalents are formed by growing smooth muscle cells within the lattice and wrapping the aggregate about a glass rod or other mandrel and then plating fibroblast and endothelial cells on the outer and inner layer, respectively, of the product obtained. Gland/organ equivalents are formed by introducing glandular cells of the specific type required into the lattice. Bone equivalents can be formed by incorporating demineralized bone powder into the hydrated lattice contracted with fibroblast cells, the required shape being produced by the mold in which the aggregate is cast.

U.S. Pat. No. 5,015,584 issued on May 14, 1991 to Miriam M. Brysk discloses an epidermal graft system wherein epidermal cells are cultured in an appropriate medium and when sufficient for the purpose, they are enzymatically detached from the container and laid on a collagen coated dressing.

These patents, and other analogous known methods of skin autografting, allografting, and xenografting may represent progress in the field of wound coverage, but do not provide an optimal, or in some cases, a variable alternative as a medical treatment for many skin injuries. Much of the prior art is dependent on complex lab procedures involving equipment that might not be available in some parts of the world, or in certain crises or disasters. Moreover, none of these, either taken singly or in combination, disclose the novel tissue-equivalent membrane produced by the process disclosed herein form an esophagus of bovine origin.

SUMMARY OF THE INVENTION

This invention is intended for the treatment of extensive wounds which involve injury to a significant area of human skin, and, in particular, to cases involving massive burns. For such injuries, a surgeon must overcome a possible lack of available donor sites, and supply the patient with appropriate temporary coverage to reduce morbidity and mortality, until further autografting using the available donor sites is possible. Additionally, the presence of an open wound, especially burns, is associated with a loss of fluid, electrolytes, proteins, and other nutrients, bringing on shock, and increasing the risk of death. Accordingly, the principal object, advantage and feature of this invention is to provide an effective treatment of such wounds, reestablishing an epithelial continuity at the wound site while healing takes place, or further autografts are contemplated.

Another object, advantage and feature of the invention is to provide an improved biological dressing for wound coverage which adheres to the underlying wound bed, provides water vapor transport, has elasticity and durability, creates a bacterial barrier, has no toxicity or antigenicity, has ease of application and removal, has a long shelf life, has minimal storage requirements, and is of low cost to produce.

A further object, advantage and feature of the invention is to provide a xenograft membrane structure similar to that of human skin: the stratified squamous epithelium corresponds to the epidermal layer of the living body.

Still a further object, advantage and feature of the invention is to provide a xenograft membrane having a low level of immunogenic activity when placed on a graft bed, resulting in the multiplication of the epidermal cells in an accelerated manner because of the adhesion effect and the absence of rejection of the xenograft.

Still a further object, advantage and feature of the invention is to provide a mucous membrane of bovine origin, produced by the method disclosed herein, which is used as skin graft material and to establish temporary wound coverage.

Still another object, feature, and advantage of the invention is to provide a xenograft membrane where the precursor, or raw material from which the invention is made is commonly available.

And, lastly, another object, advantage and feature of the invention is to provide this heterograft membrane by extraction from the esophagus of bovine origin, prepared by the method disclosed herein.

DETAILED DESCRIPTION OF THE PREFERRED EMBODIMENT

In the practice of the present invention, xenograft (heterograft) is obtained from animals, and in particular from the mucous membranes of bovine esophageal tissue. This mucous membrane tissue is distinguished from the remaining components of the esophagus in that it has a firm, rubbery consistence and a whitish tint; it has a thickness commonly in the range from about 0.2 to 0.3 millimeters, and is generally 33 to 34 inches in width.

In the preferred embodiment of the invention, and the sole example provided herein, these membranes are obtained by suitable extraction from bovine esophagus by the following method. The mucosal layers are mechanically separated from the underlying muscle tissue, and then cut into pieces having a length of about 8 inches. Using aseptic techniques, the pieces are passed through three (3) rinses of sterile isotonic saline solution and one (1) rinse of 0.02% sodium hypochlorite, and finally, an additional rinse of saline solution prior to packaging in a hermetically sealed enclosure. The enclosure is then stored at 4 degrees centigrade for clinical use. The tissue may be used for grafts on human or other animals.

The surgical procedure for therapeutic use on humans should preferably be performed on anesthetized patients. Prior to placing the tissue as a graft on a wound, the wound area should be treated by the removal therefrom of dirt, debris, hair and unwanted layers of the full thickness skin. The wound site is then washed with surgical soap and saline solution. The tissue membrane is soaked in a salt solution and is initially cut in a shape to fit the designated wound. It is the placed with the mucous side facing outward and the remaining layer side facing inward in direct contact with the wound area (graft bed). In that the membrane exhibits affinity for wet surfaces, it quickly becomes adhered to the wound. The graft then is overlaid with nylon mesh, and the injured area is bandaged with FASTANET or other suitable bandage material.

These bandages are removed four days after grafting the membrane, which is at this point, has adhered to the wound tissue. The graft remains in position for at least a week, allowing the spread of epidermal cells in the injured area. The graft will appear whiter than the surrounding skin. After a period of about 12 days, the membrane will, in part at least, slough off.

Although these grafts persist for a long period of time, in many cases a second application, or even more may be required.

In that the present invention provides stratified, squamous epithelium corresponding to the epidermal layer of the living body, it functions in the same manner as natural skin in the course of healing, without any tissue rejection reactions. The membrane becomes sufficiently adhered to the graft bed so that the graft becomes thoroughly integrated at all levels within four days, and will promote the regeneration of the dermis and epidermis from the surrounding normal tissue or can help prepare the wound area for homografting.

Other uses of the product of the present invention will be apparent to the skilled artisan, for example, for transplantation to patients undergoing surgical oncology, patients having external wounds other than burn wounds, and patients having chronic venous ulcers. The examples discussed herein are by no means limiting on the scope of the invention as defined in the claims appended hereto, and all processes, products, and uses for said invention, within the spirit of the claims, are considered to be within the scope of the invention.

What is claimed is:

1. A method of treating a skin wound with a sterile bovine esophageal tissue dressing comprising:
   treating a surface area encompassing said skin wound with an antiseptic to produce a cleansed graft zone;
   cutting the sterile bovine esophageal tissue into a planar shape having a size substantially corresponding with said cleansed graft zone; and
   layering said sterile bovine tissue dressing onto said cleansed zone area to produce a dressed zone.

2. The method according to claim 1 wherein the sterile bovine esophageal tissue dressing is produced by:
   manually separating a mucous membrane layer from esophageal tissue of bovine origin; and
   aseptically rinsing the mucous membrane layer with an antiseptic rinsing solution.

3. The method according to claim 1 which further comprises overlaying said dressed zone with a bandage.

4. The method according to claim 1 wherein the skin wound is a burn.

* * * * *